United States Patent [19]

Pisani et al.

[11] Patent Number: 4,743,443
[45] Date of Patent: May 10, 1988

[54] TRI-COLOR LIPSTICK AND METHOD OF MAKING SAME

[75] Inventors: Arthur Pisani; Robert Pisani, both of Kinnelon, N.J.

[73] Assignee: Cavalla, Inc., Hackensack, N.J.

[21] Appl. No.: 45,573

[22] Filed: May 4, 1987

[51] Int. Cl.⁴ .................................................. A61K 7/00
[52] U.S. Cl. ........................................ 424/63; 424/64; 424/DIG. 5
[58] Field of Search ...................... 424/63, 64, DIG. 5

[56] References Cited

U.S. PATENT DOCUMENTS 1,320,855 11/1919 Henderson ............... 424/DIG. 5 X
2,523,683 9/1950 DeMario ................. 424/DIG. 5 X
3,201,314 8/1965 Morshauser et al. ................. 424/64
3,479,429 11/1969 Morshauser et al. ................. 424/63
4,202,879 5/1980 Shelton ..................... 424/DIG. 5 X
4,291,018 9/1981 Oeda et al. ............................. 424/64

Primary Examiner—Nancy A. B. Swisher
Attorney, Agent, or Firm—Charles E. Temko

[57] ABSTRACT

A tri-color or alternating bi-color lipstick and method of molding the same is disclosed. The lipstick is formed using a known book-type mold. The color divisions are achieved by using a removable insert. One insert is used to form the middle section. Another insert is a solid plate and is used to prevent lipstick product from entering the middle section while the outer sections are being filled. In use, the lipstick is axially rotated by the user to present the desired color to the lips. In serial or simultaneous fashion, more than one color may be applied to permit blending.

3 Claims, 1 Drawing Sheet

FIG.1
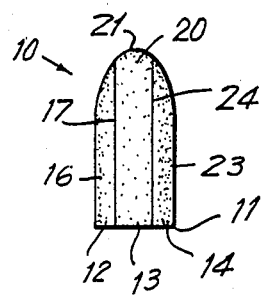
FIG.2
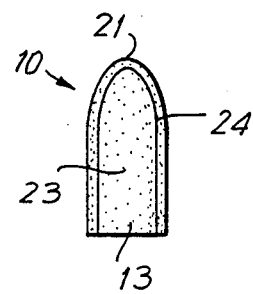
FIG.3
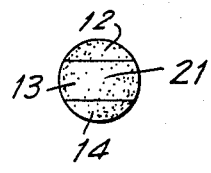
FIG.4
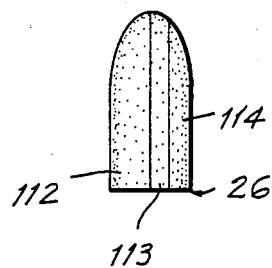
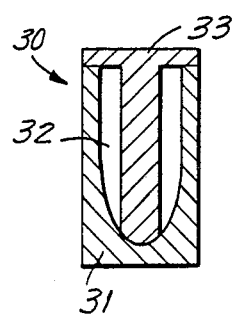
FIG.5
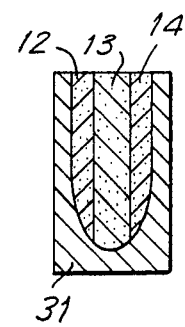
FIG.6

TRI-COLOR LIPSTICK AND METHOD OF MAKING SAME

BACKGROUND OF THE INVENTION

This invention relates generally to the field of cosmetics, and more particularly to an improved tri-color or alternating bi-color lipstick permitting the user to apply a variety of colors or blends of colors to the lips from a single lipstick.

While it is common for users to possess a variety of individual lipsticks of varying colors and shades, for use on particular occasions, it is not convenient to carry a plurality of lipsticks in a handbag, given the many other articles that are normally carried at the same time. Where different shades or types of lipcover are used simultaneously, it is often desirable to obtain a simultaneous application and blending which is not readily achieved where the user must employ several lipsticks in serial fashion.

It is also known in the art to provide composite lipsticks of a type in which one component forms a solid tubular core which is surrounded by a hollow sheath of lipstick material having a viscosity substantially less than that of the core. These constructions are not concerned with the provision of multiple colors, but rather the support of the less viscous phase so that it may be conveniently spread upon the lips by the user. Of necessity, portions of both the core and the sheath are contacted by the lips of the user when the end of the lipstick is applied.

As disclosed in U.S. Pat. No. 3,479,429, it is also known to form a unitary lipstick having a multicolored variegated pattern of color. Such a lipstick is capable only of dispensing all of the colors simultaneously without the possibility of using the colors individually.

SUMMARY OF THE INVENTION

Briefly stated, the invention contemplates the provision of an improved molded lipstick of the class described in which the above described disadvantages have been eliminated. To this end, there is provided a composite lipstick having three distinct longitudinally extending laminae which are individually poured to provide a composite tubular stick in which individual portions of the outer surface may be placed in contact with the lips of the user in a selective fashion to permit the dispensing of one desired color at a time.

BRIEF DESCRIPTION OF THE DRAWING

In the drawing, to which reference will be made in the specification, similar reference characters have been employed to designate corresponding parts throughout the several views.

FIG. 1 is a side elevational view of a first embodiment of the invention.

FIG. 2 is a second side elevational view thereof as seen from the right-hand portion of FIG. 1.

FIG. 3 is an outer end elevational view thereof.

FIG. 4 is a side elevational view corresponding to that seen in FIG. 1, but showing an alternate form of the embodiment.

FIG. 5 is a sectional view showing a first step in the molding of the embodiment shown in FIG. 1.

FIG. 6 is a sectional view showing a second and final step.

DETAILED DESCRIPTION OF THE DISCLOSED EMBODIMENT

In accordance with a first embodiment of the invention, the lipstick, generally indicated by reference character 10 comprises a composite body 11 of lipstick material formed from first, second and third parallel laminae, 12, 13 and 14, respectively.

The first lamina 12 includes an exposed outer surface 16 having a curvilinear border 17 abutting the second lamina 13.

The second lamina 13 is generally medially disposed, and has a U-shaped exposed outer surface 20, the outermost portion 21 of which extends past the outer ends of the first and third laminae 12 and 14.

The third lamina 14 may resemble in configuration that of the first lamina 12, and includes an exposed outer surface 23 and curvilinear border 24.

In the alternate form of the embodiment seen in FIG. 4, and generally indicated by reference character 26, parts corresponding to those of the principal form have been designated by similar reference characters with the additional prefix "I". The alternate form differs from the first form in that the first lamina 112 is appreciably thicker, and comprises approximately one-half of the total mass or volume of the entire lipstick. The second and third laminae 113 and 114 are both disposed entirely on one side of a longitudinal plane coincident with the principal axis of the lipstick. This form permits the first lamina to contain the commonly used shade of red, with the second and third laminae being formed of lesser used colors, for example, white frosting, or another primary color.

The lipstick is used in a manner which will be apparent from a consideration of the drawing. Colors from the first and third laminae are obtained by applying the side of the lipstick, rather than the free end thereof to the lips of the wearer, and the lipstick is rotated by the user to present the desired color. The color contained in the second lamina is applied from the free end of the lipstick, except where a color blending is desired, in which event, it is applied from the side surface of the lamina in combination with contact of the side surfaces of one or more of the first and third laminae.

FIGS. 5 and 6 illustrate a simple form of molding of both the embodiment 10 and the embodiment 26. Reference is made to British Pat No. 2,014,852 which shows a molding means for forming the usual core and sheath type of lipstick by means of an insert in the mold which permits the pouring of the components separately.

In the present case, the mold 30 includes a main body 31 forming a cylindrical cavity 32. Initially, a centrally disposed insert 33 is placed within the mold, and the first and third laminae 12 and 14 are poured, the insert maintaining a space for the later pouring of the second lamina 13. As contrasted with the mold structure in the above-mentioned British patent, the inserts are not cylindrical, but are planar to correspond to the shape of the desired lamina. By forming the insert of tapering cross section, it is possible to enlarge the area of the outermost point 21 of the second lamina 13, where desired.

It may thus be seen that there has been provided an improved lipstick of tri-color or alternating bi-color type which enables a user to have the convenience of three separate lipsticks of varying color with the cost and bulk of only a single lipstick. The use of the device is facilitated as contrasted with the serial use of several lipsticks, in that color blending may be simultaneously performed with application of lipstick material to the lips of the user.

It is to be understood that it is not considered that the invention is limited to the precise details of structure shown and set forth in this specification, for obvious modifications will occur to those skilled in the art to which the invention pertains.

What is claimed is:

1. An improved lipstick comprising a cylindrical body of lipstick material having a principal longitudinal axis, said body comprising three planar laminae in mutually parallel abutted relation, the planes of which are parallel to said longitudinal axis, said laminae each being of a different color with respect to that of an immediately adjacent lamina.

2. A lipstick in accordance with claim 1, further characterized in said cylindrical body tapering to a rounded end, whereby a medially disposed lamina extends outwardly past the borders of adjacent lamina on either side thereof.

3. A lipstick in accordance with claim 1, further characterized in one non-medially disposed lamina comprising approximately fifty percent of the mass of said lipstick.

* * * * *